US006478769B1

(12) United States Patent
Parker

(10) Patent No.: US 6,478,769 B1
(45) Date of Patent: Nov. 12, 2002

(54) ANATOMICAL FLUID EVACUATION APPARATUS AND METHOD

(75) Inventor: L. Joseph Parker, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/511,424

(22) Filed: Feb. 22, 2000

(51) Int. Cl.$^7$ .......................... A61M 31/00; A61M 5/32; A61M 1/00
(52) U.S. Cl. .......................... 604/66; 604/540; 604/272; 604/65
(58) Field of Search .................. 604/540, 541, 604/543, 65, 66, 67, 272; 600/554, 373, 546, 547, 587

(56) References Cited

U.S. PATENT DOCUMENTS

| | | | |
|---|---|---|---|
| 3,565,058 A | | 2/1971 | Mansfield |
| 4,215,699 A | * | 8/1980 | Patel .......................... 116/270 |
| 4,535,773 A | * | 8/1985 | Yoon .......................... 604/51 |
| 4,636,197 A | * | 1/1987 | Chu .......................... 604/131 |
| 5,063,370 A | * | 11/1991 | Smith .......................... 340/540 |
| 5,520,650 A | | 5/1996 | Zadini et al. |
| 5,643,197 A | | 7/1997 | Brucker et al. |
| 5,749,914 A | | 5/1998 | Janssen |
| 5,782,760 A | | 7/1998 | Schaer |
| 5,800,494 A | | 9/1998 | Campbell et al. |
| 5,827,216 A | | 10/1998 | Igo et al. |
| 5,853,373 A | * | 12/1998 | Griffith .......................... 600/554 |
| 5,954,701 A | * | 9/1999 | Matalon .......................... 604/272 |
| 5,960,797 A | * | 10/1999 | Kramer .......................... 604/272 |
| 5,997,502 A | * | 12/1999 | Reilly .......................... 604/67 |
| 6,156,009 A | * | 12/2000 | Grabek .......................... 604/117 |
| 6,162,195 A | * | 12/2000 | Igo .......................... 604/164 |

FOREIGN PATENT DOCUMENTS

DE   4420232 A 1   * 12/1995

OTHER PUBLICATIONS

Suehiro, Et Al., "Echocardiography–Guided Pericardiocentesis with a Needle Attached to a Probe," Ann Thorac Surg, Elsevier Science Inc., pp. 741–742, (Nov. 3, 1996).
Tweddell, Et Al., "Pericardiocentesis Guided by a Pulse Generator," J Am Coll Cardiol, American College of Cardiology, pp. 1074–1083, (Nov. 3, 1989).
Kerber Et Al., "Electrocardiographic Indications of Atrial Puncuture during Pericardiocentesis," New England J Med, vol. 282 (No. 20), pp. 1142–1143, (May 14, 1970).
Gotsman, Et Al., "A Pericardiocentesis Electrode Needle," Brit. Heart J., p. 566–569, (Nov. 3, 1966).
Neill, Et Al., "A Pericardiocentesis Electrode," Med Intelligence, vol. 264 (No. 14), p. 711–712, (Apr. 6, 1961).
Bishop, Jr. Et Al., "The Electrocardiogram as a Safeguard in Pericardiocentesis," J Am Med Assoc, American Medical Association, vol. 162 (No. 4), p. 264–265, (Sep. 22, 1956).

* cited by examiner

Primary Examiner—Ira S. Lazarus
Assistant Examiner—Tu Cam Nguyen
(74) Attorney, Agent, or Firm—J. Charles Dougherty

(57) ABSTRACT

An apparatus and method for evacuating an anatomical fluid from a body cavity is disclosed. The disclosed apparatus and method is particularly useful in the performance of a pericardiocentesis procedure under emergency conditions. The apparatus consists of a needle and an integrated alarm that uses the needle tip as the probe for a current sensor. As the needle tip approaches conductive media, such as myocardial tissue, the audible alarm sounds, thereby warning the operator to stop the progress of the needle to prevent contact with such tissue.

16 Claims, 3 Drawing Sheets

ANATOMICAL FLUID EVACUATION APPARATUS AND METHOD

BACKGROUND OF THE INVENTION

The present invention relates to an apparatus and method for evacuating anatomical fluids while preventing the puncture of underlying tissue, and especially relates to an apparatus and method for performing pericardiocentesis in response to emergent cardiac tamponade or other emergency conditions where pericardiocentesis is indicated.

Percardiocentesis, or pericardial tap, is the removal of fluid from the pericardial sac through a needle lumen. The pericardium is a fibrous organ that surrounds and encapsulates the heart. Under normal conditions, the pericardium is filled to a moderate pressure with a clear anatomical fluid. The function of the pericardium is to prevent dilatation of the heart chambers, to lubricate the surface of the heart, and to maintain the heart in its normal fixed position. The pericardium also functions to prevent the spread of infection from adjacent tissue to the heart, and prevents the adhesion of other tissues to the heart. The epicardium is the visceral portion of the pericardium that lies closest to the heart surface.

Pericardiocentesis may be indicated for numerous reasons. Pericardiocentesis is useful, for example, to withdraw fluids from the pericardium for study and analysis to assist in the diagnosis of pericardial diseases. In some cases, the patient upon whom diagnostic pericardiocentesis will be performed will be administered medication to prevent vasovagal reflex resulting in bradycardia (a slowing of the heartbeat) or hypotension (low blood pressure). The needle is inserted just below the sternum with a local anesthetic applied. As the needle is pushed forward into the pericardial sac, the fluid is withdrawn using the syringe attached to the needle. In some cases, an indwelling pericardial catheter may be placed in the patient for continuous drawing of the pericardial fluid for periodic analysis.

Another application for pericardiocentesis is the infusion of therapeutic agents into the pericardium for the treatment of disease. Generally speaking, however, intrapericardial injection of drugs is limited to the treatment of abnormal pericardial conditions and diseases, such as malignant or loculated pericardial effusions and tumors. Drugs that have been injected into the pericardium through pericardiocentesis include antibiotics, antineoplastic drugs, and radioactive agents. It is believed that a relatively low percentage of all pericardiocentesis procedures performed today are undertaken for this purpose. Intrapericardial drug delivery has not been utilized to treat heart-specific conditions because the pericardial space is quite small and difficult to access without invasive surgery, and the risk of cardiac injury through traditional pericardiocentesis techniques is quite high.

A third application of pericardiocentesis is the withdrawal of pericardial fluid for the treatment of acute cardiac tamponade. Acute cardiac tamponade occurs when fluid builds up within the pericardium sac, which leads to compression of the heart. As effusion fluid builds up within the pericardium, the fluid may exert sufficient pressure on the heart muscle to prevent it from pumping blood, thereby leading to the death of the patient. Cardiac tamponade is suggested by the findings of hypotension, increased central venous pressure, pulsus paradoxus, loss of the apical impulse, and distant heart sounds. Cardiac tamponade may occur due to medical causes, or may be the result of surgical procedures, such as in the case of postoperative anticoagulation or postpericardiotomy syndrome. Since patients requiring pericardiocentesis to relieve acute cardiac tamponade are often treated under emergency conditions with the patient near death as the procedure is performed, immediate diagnosis and administration of effective treatment is imperative.

A significant risk associated with the use of pericardiocentesis is the puncture of the myocardium (heart wall), a coronary artery, or the walls of other nearby organs, such as the lung, liver, or stomach. Because the pericardial space is quite small, it is difficult for the physician performing pericardiocentesis to accurately determine when the fibrous pericardium wall has been breached by the needle, while simultaneously preventing contact between the distal end of the needle and the myocardium. In an adult patient, 5–10 mm may be sufficient penetration beneath the skin to reach the pericardial fluid, but this number is highly variable based on the patient's height, weight, and condition. The physician performing this procedure inserts the needle immediately to the left of the xiphisternum and towards the tip of the left scapula, slowly drawing backward on the plunger of the syringe to which the needle is attached. The physician stops the advance of the needle when pericardial fluid is seen to begin collecting in the syringe. If, however, the physician does contact or puncture the myocardium, the result may be myocardial infarction, need-induced arrhythmias, ventricular fibrillation, or even acute cardial tamponade, any of which can lead to the death of the patient. One study reports that, although exact figures concerning the incidence of acute cardial tamponade as a result of pericardiocentesis are not known, the majority of one group of prominent cardiologists and surgeons had personal knowledge of one or two such incidents. Linton H. Bishop, Jr., et al., *The Electrocardiogram as a Safeguard in Pericardiocentesis*, 162 J.A.M.A. 264 (Sept. 22, 1956). Because of the high risk associated with emergency-room use of pericardiocentesis to relieve acute cardiac tamponade, the procedure is currently performed only when the life of the patient is perceived to be immediately at stake.

A number of methods have been suggested to reduce the risk of contacting or puncturing the myocardium during pericardiocentesis. One method is to combine two-dimensional echocardiography with the pericardiocentesis procedure. Shigefumi Suehiro, et al., *Echocardioranphy-Guided Pericardiocentesis with a Needle Attached to a Probe*, 61 Ann. Thorac. Surg. 741 (1996) discloses an echocardiographic probe with an attached pericardiocentesis needle for this purpose. The tip of the pericardial needle is scratched with a scalpel to improve the echo-return intensity of the needle. When the needle is inserted to perform the pericardiocentesis procedure, the tip of the needle can be seen on the echocardiograph monitor. The operator may thereby visually determine the position of the needle tip relative to the heart. Although Suehiro discloses that the procedure may be performed with one operator, such an operator would be required to divert his or her attention from the insertion of the needle to observe the echocardiography monitor.

Another method to reduce the risk of puncturing the myocardium during a procedure to access the pericardial cavity is disclosed in U.S. Pat. No. 5,827,216 to Igo et al. Igo et al. discloses an apparatus and method for introducing a tube percutaneously to contact the exterior surface of the pericardium. A vacuum is introduced within a tube such that a bleb is formed on the pericardium surface. A needle within the tube is then advanced to puncture the pericardial bleb, while avoiding contact with the myocardium. A guide wire within the needle may then be advanced into the pericardial cavity, and may be used to guide an intrapericardial catheter for injection or infusion of therapeutic agents. Drugs may also be injected directly through the needle into the pericardial space.

Perhaps the most widely recognized method to reduce the risk of puncturing the myocardium during pericardiocentesis is to connect the patient and needle to an electrocardiograph, as described in Bishop, supra; James R. Neill, et al., *A Pericardiocentesis Electrode*, 264 N. Engl. J. Med. 711 (Apr. 6, 1961); Richard E. Kerber, et al., *Electrocardiographic Indications of Atrial Puncture during Pericardiocentesis*, 282 N. Engl. J. Med. 1142 (May 14, 1970); and Mervyn S. Gotsman & Velva Schrire, *A Pericardiocentesis Electrode Needle*, 28 Brit. Heart J. (1966). Bishop et al., for example, discloses that the lead wires of the electrocardiograph are connected to the arms and legs of the patient, while the precordial lead wire is attached to the shank of the pericardiocentesis needle by using an extra length of wire with alligator clamps at both ends. The needle becomes an exploring electrode, which feeds data back to the electrocardiograph. As the pericardiocentesis procedure is carried out, the electrocardiogram is continuously monitored by an observer other than the operator. Contact with the myocardium is indicated by the appearance of an elevation of the S-T segment if the ventricular muscle is contacted, or of the P-R segment if the auricle is contacted.

Neill et al. discloses an improvement on the Bishop et al. apparatus. The extra length of wire with two alligator clips is replaced by a collar that is in electrically conductive contact with the needle, a socket to accept the lead from the electrocardiograph, and a length of wire connecting the collar and socket. Set screws on the collar and socket hold the needle and lead, respectively, firmly in place. Once the proper depth is reached with the needle, the collar set screw is tightened. Gotsman et al. discloses another variation on this theme. Both of these devices require the use of an electrocardiograph, and thus would require an additional observer to monitor the electrocardiogram while the operator inserts the needle.

A more recently developed variation on the electrocardiograph method of pericardiocentesis is disclosed in James S. Tweddell, et al., *Pericardiocentesis Guided by a Pulse Generator*, 14 J. Am. Coll. Cardiol. 1074 (October 1989). Tweddell et al. discloses that ST segments viewed in an electrocardiogram may be altered by medications, pericarditis, ventricular hypertrophy, ischemia and infarction, which limits the usefulness of electrocardiogram monitoring of the pericardiocentesis needle as an effective safeguard. Tweddell asserts that the use of a pacing current applied to the pericardiocentesis needle will allow the operator to more accurately determine the moment when myocardial tissue is contacted. The Tweddell et al. needle is insulated with shrink-wrap Teflon along its length except the final 3 mm of the needle tip. As in other electrocardiograph methods, the operator or another observer must monitor the electrocardiogram results during the pericardiocentesis procedure.

Each of the prior art methods discussed above requires that the operator or another observer continuously monitor an external output device, such as the video display on an electrocardiogram or an echocardiography device, during the pericardiocentesis procedure. If the operator is monitoring such a device, the risk associated with the procedure is increased, since the operator must divert some of his or her attention from the insertion of the needle and the evacuation of pericardial fluid to the monitor. At best, the operator cannot devote full attention to both the operation of the pericardiocentesis needle and the monitor simultaneously. If a second observer is used to observe the monitor on the device used, then a second trained individual is necessary for the performance of this procedure. In addition to increasing the cost of the procedure, the requirement of two trained persons reduces the applicability of the procedure to emergency situations, such as when acute cardiac tamponade occurs.

Each of the prior art methods discussed above also require bulky external equipment. In the case of the electrocardiography methods, each requires an electrocardiogram for the procedure to be performed. In the case of the echocardiography method, an external echocardiograph monitor must be used. In either case, the additional equipment increases the cost of the procedure. Also, since it necessarily takes some time to connect the pericardiocentesis needle to the external equipment, and since even seconds may be critical to the patients survival in such situations, the applicability of the prior art procedures to emergency situations is reduced.

Because of these limitations, it is common practice for physicians performing pericardiocentesis under emergency conditions to simply insert the needle percutaneously into the pericardium without the benefit of electrocardiography or echocardiography. In such situations, the physician relies merely on his or her experience and the "feel" of the needle as it is inserted, along with the observation of pericardial fluid drawn into the syringe, to gauge the point at which the needle has pierced the pericardium and thus progress must be arrested before the myocardium is pierced. With no direct means of determining the position of the needle's tip within the pericardial. sac, and considering the small area within the pericardial sac and the likelihood of injury or death if the myocardium is contacted, this method significantly increases the risk associated with pericardiocentesis. In fact, it is believed that roughly 40% of all pericardiocentesis procedures performed without direct monitoring of the needle tip result in a puncturing of the myocardium. As herein explained, the puncture of the myocardium can have numerous deleterious effects and even death of the patient. The results of myocardial injury are often magnified in emergency situations, since the patient may be experiencing other trauma, particularly cardiac trauma, at the time that the pericardiocentesis is performed. Thus a direct method of monitoring the position of the needle tip with respect to the myocardium, which does not require bulky external equipment or an additional observer, is desired.

SUMMARY OF THE INVENTION

The present invention is an apparatus and method for performing pericardiocentesis safely under emergency conditions, such as in the case of acute cardial tamponade. The apparatus consists of a needle designed for pericardiocentesis with an integrated current- and voltage-sensing mechanism and alarm. The device may be powered by a stored energy source, such as one or more watch batteries, so that no external cords or wires are required for power. Connected in a series circuit with the power source is a gated current and voltage sensor, which is connected through a wire lead to the needle. An audio alert mechanism, such as a piezoelectric speaker, is also connected in series in this circuit.

By simply responding to the audible alert produced by the device, the operator may directly determine the position of the needle tip without the need of external monitors or bulky electrocardiography or echocardiography equipment.

Moreover, only a single operator is required since the operator need not divert his or her attention from the insertion of the needle to listen to the audible alarm. Because the disclosed device requires no external wires or connections, and is entirely self-contained, the device is ideal for emergency conditions or when full hospital facilities are unavailable. In addition, because the device may be constructed inexpensively from standard electronic components, it may be assembled with a minimum of manufacturing cost.

It is an object therefore of the present invention to provide an apparatus and method for performing pericardiocentesis with greatly reduced risk of piercing the myocardium or other body tissues.

It is a further object of the present invention to provide an apparatus for performing pericardiocentesis without the necessity of bulky, external, expensive equipment in order to directly detect the position of the needle tip within the pericardial sac.

It is a still further object of the present invention to provide an apparatus and method for performing pericardiocentesis under emergency conditions.

It is a still further object of the present invention to provide an apparatus and method for performing pericardiocentesis requiring only one operator whose attention need not be diverted from the insertion of the pericardiocentesis needle into the patient.

Further objects and advantages of the present invention will be apparent from a consideration of the following detailed description of the preferred embodiments in conjunction with the appended drawings as briefly described following.

DETAILED DESCRIPTION OF THE PREFERRED EMBODIMENTS

Figure 2:
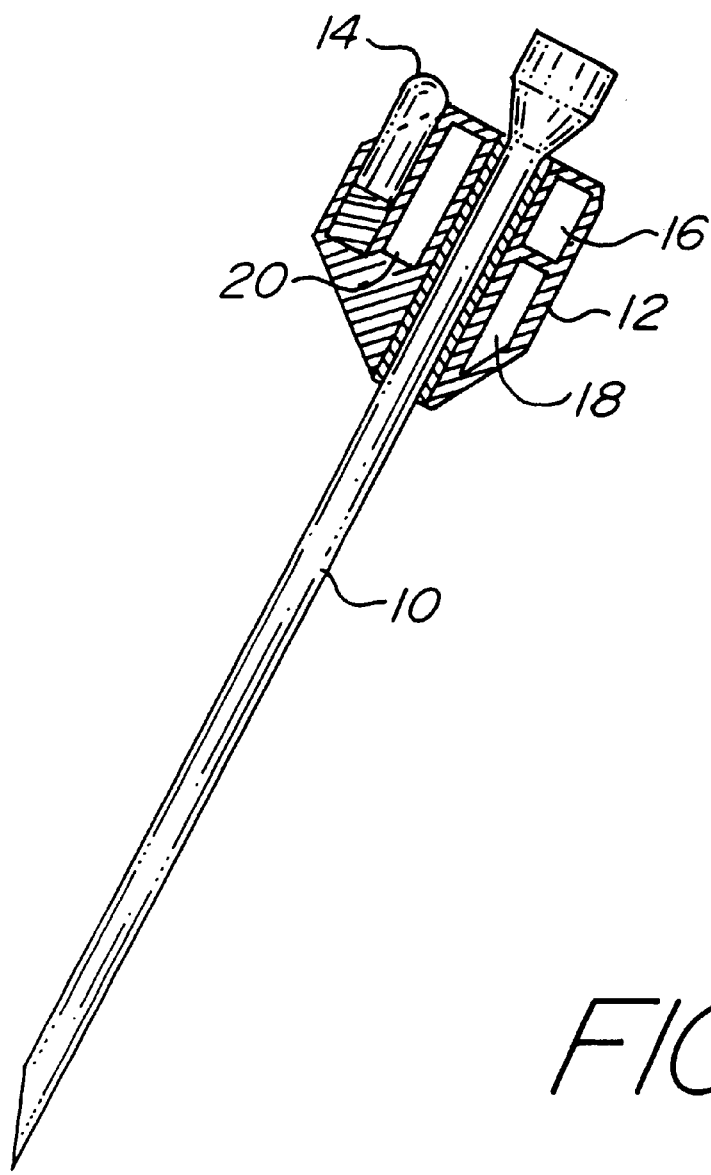
FIG. 2 is a partially cut-away elevational view of the present invention.

Referring now to FIG. 2, the construction of a preferred embodiment of the present invention may be described. Needle 10 is a standard needle of the type commonly used for pericardiocentesis procedures. Attached near the proximal end of needle 10 is housing 12. Each of the electronic components of the preferred embodiment are contained within housing 12. Extending from within housing 12 to the exterior of housing 12 is test button 14. Within housing 12 are speaker 16, current/voltage sensor 18, and battery 20. In the preferred embodiment, housing 12 may consist of two pieces that snap together such that housing 12 may be easily opened to replace battery 20 when expended.

Figure 3:
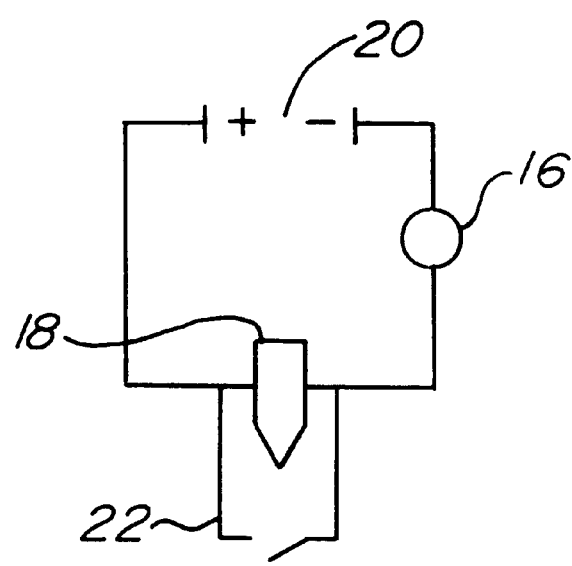
FIG. 3 is a circuit diagram of the electronic and electrical components of the present invention.

FIG. 3 is a circuit diagram for the electronic components and circuitry of a preferred embodiment of the present invention. Battery 20 provides a power source for the device. In the preferred embodiment, battery 20 may be a standard watch battery, or in an alternative embodiment may be a long-life lithium battery of the type as commonly used in cameras and video equipment.

Current/voltage sensor 18 is comprised of voltage gated and amperage gated transistors. Several manufacturers produce sensors of this type; one example is the Rainbow 100 mA Relay, product number 990-0070. Sensor 18 is connected to needle 10 through a wire lead (not shown) as is well understood in the art. Sensor 18 is chosen such that it will open only if the voltage and amperage at needle 10 exceed the threshold that is determined to be most specific to myocardial depolarization. Also, sensor 18 is chosen so that it will remain closed if the voltage and amperage at needle 10 exceed the limits produced by myocardial cells; this reduces the likelihood that the device will be activated by contact with other tissue that may carry an electrical charge, such as skeletal muscle tissue. When the amperage and voltage at needle 10 exceed the threshold but do not exceed the limit values, sensor 18 will open and thereby allow current to flow through the circuit of FIG. 2.

When current flows through the circuit of FIG. 2, speaker 16 is activated and provides an audible alert to the operator. Speaker 16 may be of any standard variety, such as a piezoelectric speaker. In an alternative embodiment, a light-emitting diode (not shown) as is well understood in the art may be inserted in the circuit of FIG. 2, either in place of speaker 16 or in addition to speaker 16, to provide a visual alert as well as an audible alert to the operator.

Test button 14 is connected to switch 22 such that pressing test button 14 will close switch 22, thereby bypassing sensor 18 in the circuit of FIG. 2. Thus the result of pressing switch 22 will be a test of the charge remaining in battery 20, and a general test of the operation of the alert features of the disclosed device.

In operation, needle 10 operates as a detector for conductive media, particularly myocardial tissue. As the tip of needle 10 approaches myocardial tissue, sensor 18 opens and allows current to flow to speaker 16 from battery 20, thereby creating an audible alarm.

Figure 1:
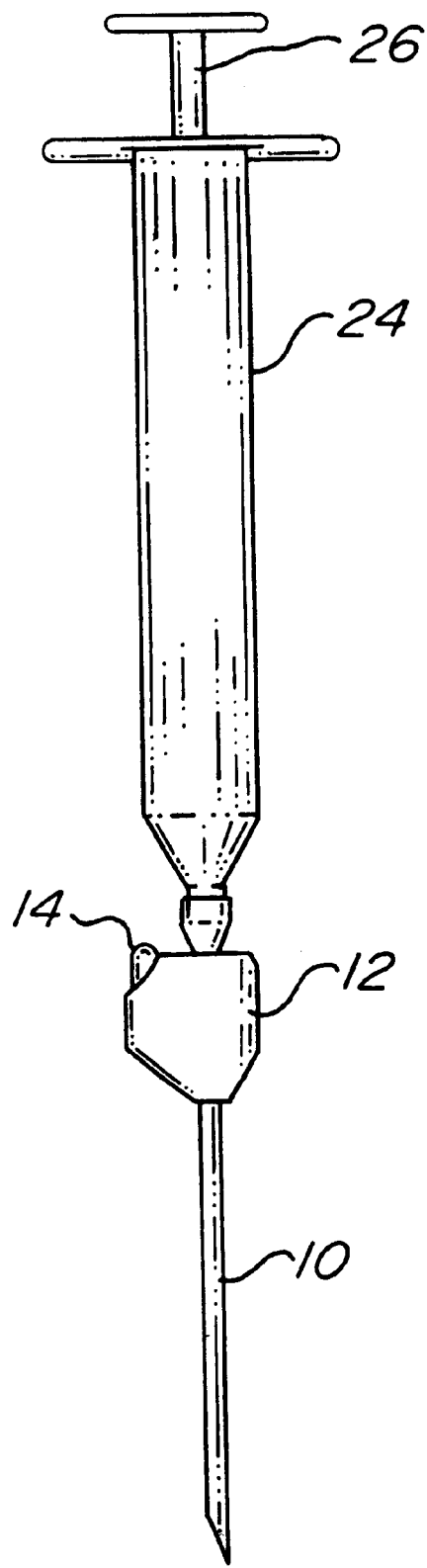
FIG. 1 is a side elevation of the present invention with an attached syringe.
Figure 4:
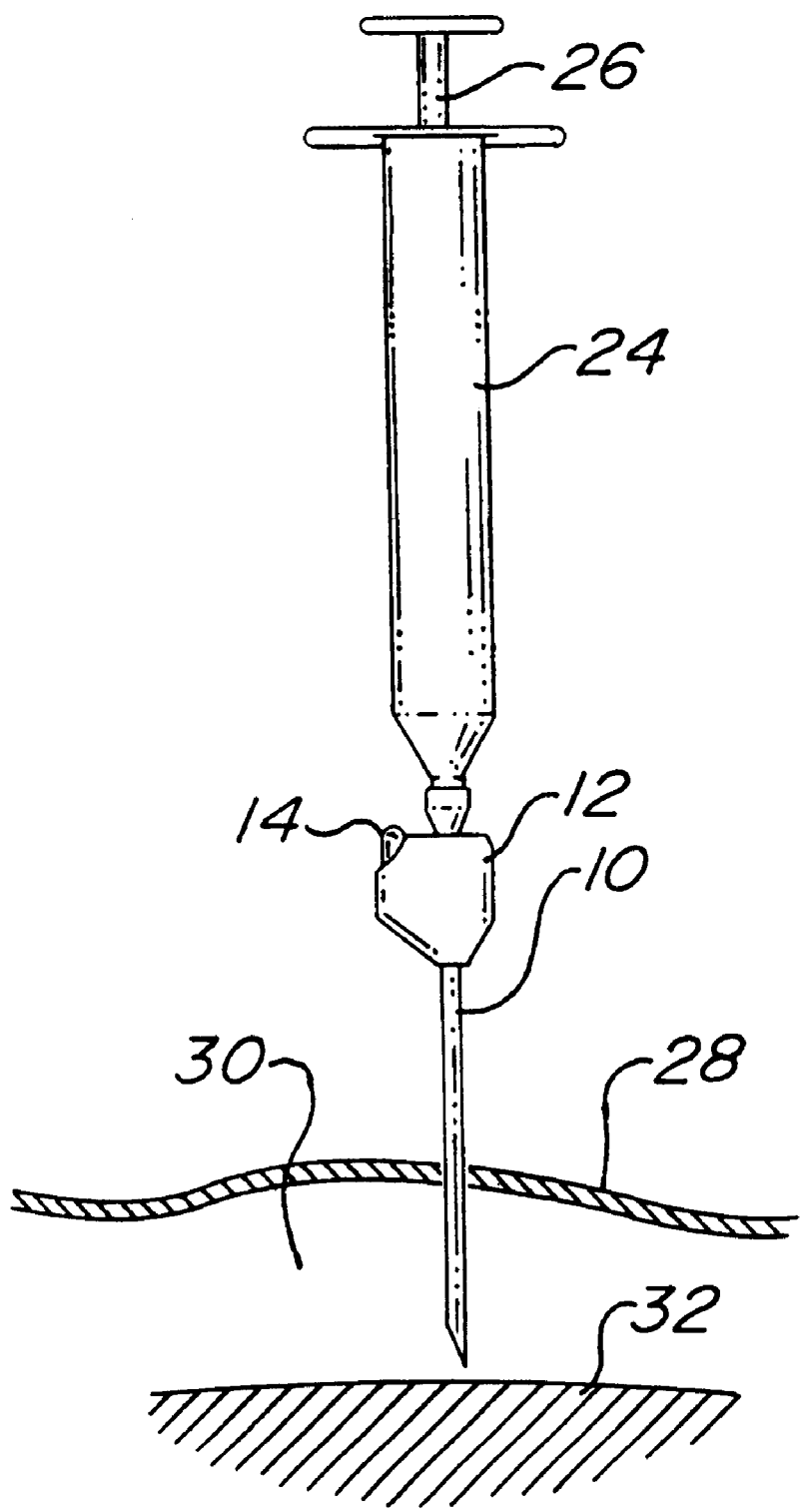
FIG. 4 is an illustration of the present invention with an attached syringe shown drawing fluid from the pericardial sac during a pericardiocentesis procedure.

To perform pericardiocentesis using the preferred embodiment of the disclosed invention, needle 10 is attached to syringe 24 as shown in FIG. 1. A test is performed for the function of the device, as explained above, by depressing test button 14 and noting whether the audible alert from speaker 16 is activated. If the test indicates that the device is working properly, needle 10 is then inserted percutaneously as in a traditional pericardiocentesis procedure, as shown in FIG. 4.

The pericardium 28 is fibrous and is a relatively poor conductor of electricity, and thus sensor 18 will have input voltage and amperage below its threshold level while needle 10 passes through pericardium 28. As a result, speaker 16 will not be activated at this stage. Because of its structure, myocardium tissue is highly conductive, and thus as the tip of needle 10 passes through the pericardial sac 30 and approaches myocardium 32, the current and amperage level input to sensor 18 will pass the threshold level, sensor 18 will open, and current will flow from battery 20 to speaker 16, thereby activating speaker 16. The audible alarm produced thereby will warn the operator that the tip of needle 10 is near myocardial tissue, and thus further progress of needle 10 should be halted. The operator may then begin to remove fluid from pericardial sac 30 by pulling plunger 26 toward the operator, thereby drawing fluid from pericardial sac 30, through needle 10, and into syringe 24.

It should be understood that any theories of operation provided herein may be incomplete or inaccurate without limiting the results described and the invention claimed below. The present invention has been described with reference to certain preferred and alternative embodiments which are intended to be exemplary only and not limiting to the full scope of the present invention as set forth in the appended claims.

What is claimed is:

1. An apparatus for the evacuation of fluids from an anatomical cavity, said apparatus comprising:
   a) a needle having a proximal and distal end;
   b) a power source in electrical communication with said needle;
   c) a sensor in electrical communication with said needle and said power source, wherein said sensor is operable to discriminate between myocardial tissue and non-myocardial tissue; and
   d) an alarm in electrical communication with said sensor.

2. The apparatus of claim 1, wherein said alarm is activated when the distal end of said needle approaches myocardial tissue.

3. The apparatus of claim 2, wherein said alarm is a piezoelectric speaker.

4. The apparatus of claim 3, wherein said electric power source is at least one battery.

5. The apparatus of claim 4, wherein said at least one battery comprises a watch battery.

6. The apparatus of claim 2, further comprising:
   a) a switch in communication with said power source; and
   b) a test button in communication with said switch.

7. The apparatus of claim 6, further comprising a housing connected to said needle near the proximal end of said needle, said housing providing a mounting point for said power source, said alarm, and said test button.

8. The apparatus of claim 7, further comprising a syringe connected to the proximal end of said needle.

9. The apparatus of claim 8, further comprising electrical wiring connecting said needle, said power source, said alarm, and said test button.

10. A method for evacuating fluids from an anatomical cavity while avoiding the penetration of myocardial tissue, said method comprising the steps of:
    a) inserting a needle into the cavity, said needle having a proximal and distal end, said needle connected to an electrical power source, a current sensor connected to said power source wherein said sensor is operable to discriminate between myocardial tissue and non-myocardial tissue, and said sensor connected to an alarm;
    b) stopping the insertion of the needle when the alarm sounds;
    c) evacuating fluids from the cavity;
    d) removing the needle from the cavity.

11. The method of claim 10, wherein the anatomical cavity is the pericardial sac.

12. The method of claim 11, wherein the conductive medium is myocardial tissue.

13. The method of claim 12, wherein the alarm is a piezoelectric speaker.

14. The method of claim 13, wherein the electric power source is at least one battery.

15. The method of claim 14, wherein the at least one battery comprises a watch battery.

16. The method of claim 15, further comprising the step of activating a test button in communication with the power source prior to the insertion step.

\* \* \* \* \*